United States Patent [19]

Pujado

[11] 4,283,568
[45] Aug. 11, 1981

[54] PROCESS FOR THE RECOVERY OF PHENOL FROM A REACTION MIXTURE RESULTING FROM THE ACID CLEAVAGE OF CUMENE HYDROPEROXIDE

[75] Inventor: Peter R. Pujado, Palatine, Ill.

[73] Assignee: UOP Inc., Des Plaines, Ill.

[21] Appl. No.: 108,736

[22] Filed: Dec. 31, 1979

[51] Int. Cl.$^3$ .................. C07C 37/68; C07C 37/86
[52] U.S. Cl. .................................................. 568/754
[58] Field of Search ....................................... 568/754

[56] References Cited
U.S. PATENT DOCUMENTS

| 3,931,339 | 1/1976 | Cooke | 568/754 |
| 4,016,213 | 4/1977 | Cheen et al. | 568/754 |

Primary Examiner—Werren B. Lone
Attorney, Agent, or Firm—James R. Hoatson, Jr.; Robert W. Welch; William H. Page, II

[57] ABSTRACT

A process for the recovery of phenol from a reaction mixture resulting from the acid cleavage of cumene hydroperoxide is disclosed. Neutralization of the acidic reaction mixture is effected with sodium phenate—a product derived from the subsequent recovery of phenol and recycled to the neutralization process. Utilization of internal process recycle streams in this manner affords a reduced consumption of acid and caustic, and permits the elimination of certain vessels in the recovery scheme.

2 Claims, 1 Drawing Figure

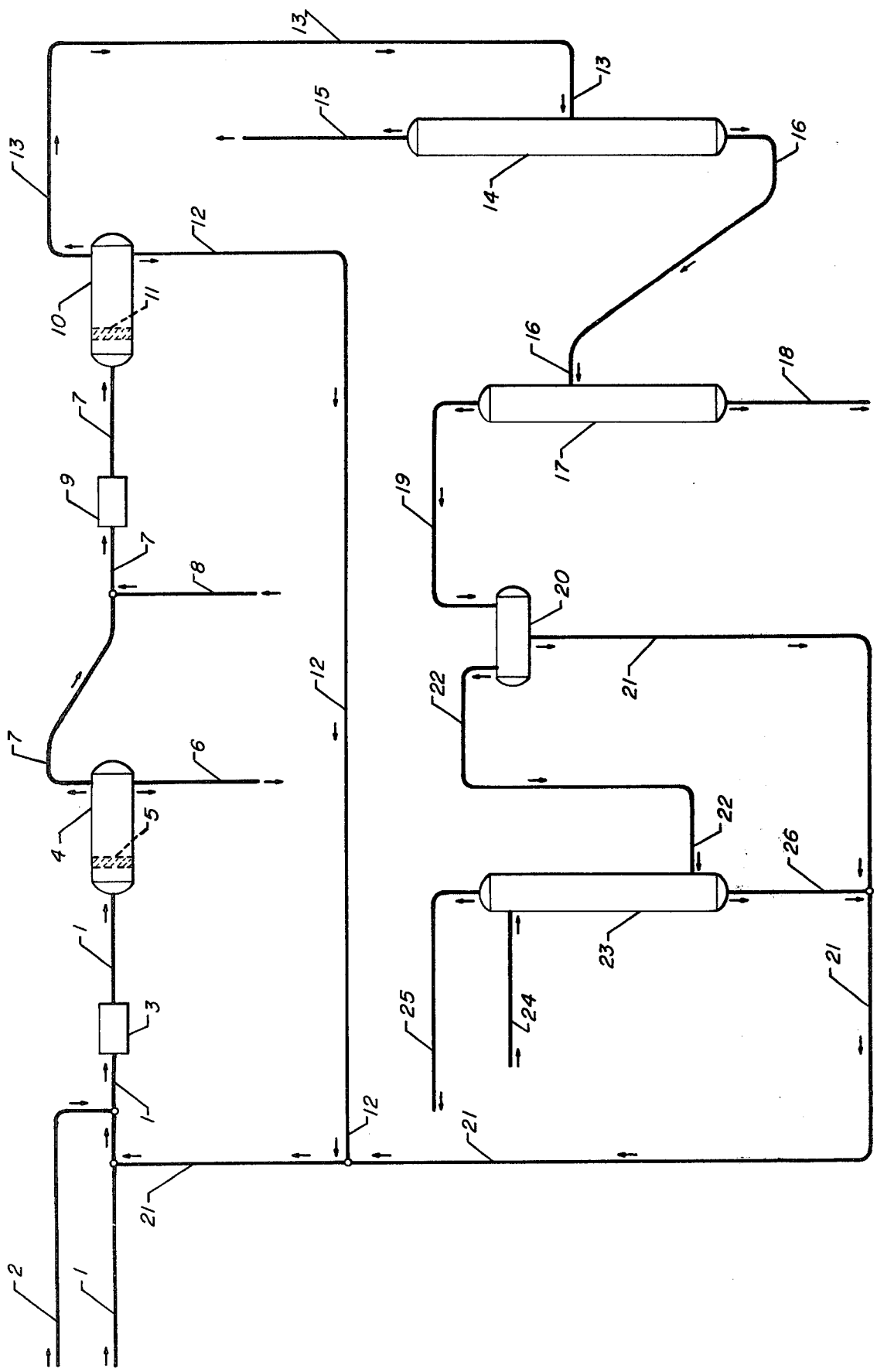

PROCESS FOR THE RECOVERY OF PHENOL FROM A REACTION MIXTURE RESULTING FROM THE ACID CLEAVAGE OF CUMENE HYDROPEROXIDE

This invention relates to a process for the recovery of a phenol from a reaction mixture resulting from the acid cleavage of an α,α-dialkylbenzyl hydroperoxide, and, in particular, to a process for the recovery of phenol from a reaction mixture resulting from the acid cleavage of cumeme hydroperoxide.

In general, phenols are prepared by the oxidation of a secondary alkylbenzene and the subsequent acid cleavage of the resulting α,α-dialkylbenzyl hydroperoxide to form a reaction mixture comprising a phenol, a ketone and unreacted secondary alkylbenzene. The present invention is particularly directed to a process wherein phenol is prepared by the air oxidation of cumene and the subsequent acid cleavage of the resulting cumene hydroperoxide to form a reaction mixture comprising phenol, acetone and unreacted cumene. In addition to the principal products, there are formed varying amounts of by-products such as mesityl oxide, α-methylstyrene, p-cumylphenol, phenyldimethylcarbinol, acetophenone, and higher molecular weight phenols.

In the process of recovering phenol from the acid cleavage reaction mixture, the acidic reaction mixture is initially neutralized, either directly by the addition of caustic, or indirectly by contact with an ion exchange resin. In any case, the neutralized reaction mixture is fed to a distillation column, commonly referred to as a crude acetone column, at conditions to effect a crude separation of those materials boiling below phenol whereby an overhead fraction is recovered comprising substantially all of the acetone and lower boiling by-products, as well as a substantial portion of the water and unreacted cumene. Acetone is subsequently recovered, as is cumene, by the further distillation of the crude acetone column overhead, the cumene being recycled to the oxidation process.

The bottoms fraction recovered from the crude acetone column, comprising phenol and α-methylstyrene as well as the balance of the water and unreacted cumene, is typically treated for the separation of heavy ends and thereafter fed to a distillation column, commonly referred to as a cumene or α-methylstyrene column. The last-mentioned column is operated at conditions to separate an overhead fraction comprising water, cumene and α-methylstyrene from the higher boiling phenol product. The phenol, recovered as the bottoms fraction, further contains certain impurities, e.g., mesityl oxide, hydroxy acetone, etc., and said impurities are treated and separated from said bottoms fraction to yield a substantially pure phenol product.

The overhead fraction from the cumene column will invariably comprise a significant amount of phenol as well as cumene and α-methylstyrene. It has heretofore been the practice to caustic-extract this overhead fraction, and the cumene/α-methylstyrene recovered as a water-immiscible organic phase is hydrotreated and recycled to oxidation as cumene. The phenol is recovered as sodium phenate in the aqueous phase, a practice which has heretofore necessitated a separate phenol recovery facility wherein the aqueous sodium phenate solution is acid treated, the resulting phenol being recycled and combined with the acid cleavage product for recovery as heretofore described, and the acidifying agent being subsequently caustic-treated for safe disposal.

In one of its broad aspects, the present invention embodies an improvement in a process for the recovery of a phenol from a reaction mixture resulting from the acid cleavage of an α,α-dialkylbenzyl hydroperoxide and comprising said phenol, a ketone and unreacted secondary alkylbenzene, which improvement comprises effecting the neutralization of said reaction mixture by admixing therewith an alkali metal phenate; recovering said ketone from the neutralized reaction mixture; separating the ketone-free reaction mixture into a phenol fraction and a secondary alkylbenzene/secondary alkenylbenzene fraction containing residual phenol; recovering said phenol fraction; treating the secondary alkylbenzene/secondary alkenylbenzene fraction with an alkali metal hydroxide and converting the residual phenol contained therein to an alkali metal phenate; separating and recycling said alkali metal phenate to effect the first-mentioned neutralization of said reaction mixture.

One of the more specific embodiments relates to a process for the recovery of phenol from a reaction mixture resulting from the acid cleavage of cumene hydroperoxide and comprising said phenol, acetone, and unreacted cumene, which process comprises effecting the neutralization of said reaction mixture by admixing therewith an aqueous sodium phenate solution; recovering said acetone from the neutralized reaction mixture; separating the acetone-free reaction mixture into a phenol fraction and a cumene/α-methylstyrene fraction containing residual phenol; recovering said phenol fraction; caustic-treating the cumene/α-methylstyrene fraction and converting the residual phenol contained therein to sodium phenate; separating and recycling said sodium phenate to effect the first-mentioned neutralization of said reaction mixture.

The overall process to which this invention pertains concerns the oxidation of a secondary alkylbenzene, for example, isopropylbenzene (cumene), isobutylbenzene, isoamylbenzene, 1-methyl-4-isopropylbenzene, p-diisopropylbenzene, p-diisobutylbenzene, 1-isopropyl-4-isobutylbenzene, and the like, to form the corresponding hydroperoxide, i.e., isopropylbenzene hydroperoxide, isobutylbenzene hydroperoxide, isoamylbenezene hydroperoxide, 1-methyl-4-isopropylbenzene hydroperoxide, p-diisopropylbenzene hydroperoxide, p-diisobutylbenzene hydroperoxide, 1-isobutyl-4-isopropylbenzene dihydroperoxide, and the like. The present invention is particularly directed to a process for the recovery of phenol from a reaction mixture resulting from the acid cleavage of isopropylbenzene hydroperoxide, more commonly referred to as cumene hydroperoxide.

The aforesaid oxidation reaction is effected at conditions well known in the art. The hydroperoxide oxidation product can be prepared by direct liquid phase oxidation of the selected alkylbenzene with oxygen, or an oxygen-containing gas such as air, usually at an elevated temperature. The oxidation reaction proceeds slowly through an initial induction period, accelerating to a more favorable rate with the formation of the hydroperoxide which exerts a catalytic effect on the oxidation reaction. This initial induction period is eliminated, or substantially reduced, by initially including a hydroperoxide in the reaction mixture, usually the hydroperoxide product of the reaction. However, other materials are disclosed in the art which exhibit a similar catalytic effect. Temperatures effecting the oxidation reaction range from about room temperature to about the boiling point of the hydrocarbon subjected to oxidation, which, in the case of cumene, is about 305° F. In general, it is preferred to utilize an elevated temperature in the range of from about 120° to about 265° F. The optimum temperature will depend on the particular alkylbenzene to be oxidized and on the reaction conditions otherwise employed. The oxidation can be effected at pressures ranging from about atmospheric to about 500 psig., although a pressure not exceeding about 90 psig. is generally preferred. It is desirable to limit the contact time of the reactants at oxidation conditions to effect substantially less than complete conversion of the alkylbenzene to the corresponding hydroperoxide. For example, in the oxidation of cumene, it is desirable to limit the contact time of the cumene and the oxidizing agent so that the concentration of the resulting cumene hydroperoxide does not exceed about 30 wt.%.

The further description of the process of this invention is presented with reference to the attached drawing. The drawing is a simplified flow diagram of a phenol recovery process representing one preferred embodiment of this invention and is not intended as an undue limitation on the generally broad scope of the invention as set out in the appended claims. Certain hardware such as valves, pumps, compressors, heat exchangers, instrumentation and controls, have been omitted as not essential to a clear understanding of the invention, the use and application of said hardware being well within the skill of the art.

Referring then to the drawing, a reaction mixture resulting from the acid cleavage of cumene hydroperoxide is charged to the phenol recovery process through line 1. In this instance, the cleavage reaction mixture comprises, on an hourly basis, about 115.8 moles of phenol, 123.8 moles of acetone, 37.9 moles of unreacted cumene, 4.8 moles of α-methylstyrene, 0.3 moles of sulfuric acid, and 29.9 moles of water. A recycle stream from line 21, originating as hereinafter described and comprising about 3.4 moles of sodium phenate and 0.5 moles of sodium hydroxide, is combined with the acid cleavage reaction mixture in line 1 whereby said reaction mixture is neutralized and said sodium phenate is recovered therein as phenol. Said recycle stream further comprises about 0.3 moles of acetone and 87.2 moles of water discharged into line 1 per hour. In this instance, about 1.6 moles of 98 wt.% sulfuric acid are metered through line 2 per hour to adjust the pH of the combined streams to a pH of about 6 or less and facilitate the subsequent separation of phenol therefrom. The resulting mixture is then continued through line 1 and a mixing means 3 to a settler 4.

In the settler 4, the mixture is processed through a coalescing means 5 to promote a separation of the organic and aqueous phases therein. The organic and aqueous phases are preferably treated at a temperature in excess of about 90° F., and more preferably at a temperature of from about 95° to about 120° F. This allows for a maximum concentration of sodium sulfate in the aqueous phase, taking full advantage of the salting-out effect of the sodium sulfate. Further, any of the sodium sulfate precipitating from the aqueous phase will do so as a free flowing anhydrous form less apt to deposit on a surface and cause the fouling of process equipment. Substantially all of the phenol is recovered in the organic phase, the recovery being facilitated by the salting-out effect of the sodium sulfate salt of neutralization recovered in the aqueous phase. About 61.2 moles of water and 1.9 moles of sodium sulfate are withdrawn from the settler 4 per hour by way of line 6 and treated for the recovery of entrained organic products in conventional recovery means which are not shown. A primarily organic phase is withdrawn from the settler 4 by way of an overhead line 7, admixed with about 25.3 moles of water per hour from line 8, and continued through line 7 and a mixing means 9 to a second settler 10 to assure the complete separation of sodium sulfate. In the second settler 10, the mixture is processed through a coalescing means 11 to facilitate the further separation of the aqueous and organic phases. About 119.1 moles of phenol, 124.1 mols of acetone, 37.9 moles of cumene, 4.8 moles of α-methylstyrene, and 85.2 moles of water are recovered from the second settler 10 through an overhead line 13 on an hourly basis, and this mixture is charged to a crude acetone column 14. The water phase from the settler 10 is recovered and recycled to the first settler 4 by way of lines 12, 21 and 1.

About 123.8 moles of acetone per hour are distilled overhead from the crude acetone column in admixture with about 9.2 moles of cumene and 46.8 moles of water per hour. This mixture, representing the bulk of the acetone produced, is taken overhead through line 15 and further treated in distillation means, not shown, for the recovery of a substantially pure acetone product—the cumene being recycled to the oxidation phase of the overall process.

A bottoms fraction, withdrawn from the crude acetone column 14 by way of line 16, is charged to a cumene column 17, said bottoms fraction comprising about 119.2 moles of phenol, 0.3 moles of acetone, 28.7 moles of cumene, 4.8 moles of α-methylstyrene and 38.4 moles of water on an hourly basis. About 115.8 moles of phenol are recovered per hour from the bottom of the cumene column 17 by way of line 18, and this product is further treated in distillation means, not shown, for the recovery of a substantially pure phenol product.

The overhead fraction, withdrawn from the cumene column 17 by way of line 19, comprises about 3.3 moles of phenol, 0.3 moles of acetone, 28.7 moles of cumene, 4.8 moles of α-methylstyrene and 38.4 moles of water per hour, and this fraction is charged to a settler 20. The aqueous phase which settles out comprises substantially all of the water charged to the settler, and this water is withdrawn through line 21 at a rate of about 38.4 moles per hour along with about 0.2 moles of phenol and 0.1 moles of acetone per hour. This material is ultimately recycled to the phenol recovery process as hereinafter described.

Substantially all of the cumene charged to the settler 20 is recovered in the organic phase which forms therein, and this cumene is ultimately recycled to the oxidation phase of the overall process. The organic phase will also comprise acetone, a substantial amount of phenol, and substantially all the α-methylstyrene charged to said settler 20. That phenol adversely affects the oxidation phase of the overall process, is well known. Therefore, in keeping with the prior art practice, the organic phase is caustic-treated whereby the phenol is converted to sodium phenate and recovered with the acetone in the resulting aqueous phase.

Referring then to the drawing, the organic phase is recovered from the settler 20 through an overhead line 22 and transferred to the bottom of a caustic wash column 23. Said organic phase provides about 3.2 moles of phenol, 0.2 moles of acetone, 28.7 moles of cumene and 4.8 moles of α-methylstyrene to the caustic wash column per hour. An aqueous caustic stream charged to the upper portion of the caustic wash column through line 24 provides about 48.8 moles of water and 3.9 moles of sodium hydroxide thereto per hour. The organic phase passes upwardly in countercurrent contact with the aqueous caustic phase and, in the process, phenol is recovered in the aqueous caustic phase as sodium phenate. Essentially all of the cumene and α-methylstyrene is recovered from the caustic wash column 23 through an overhead line 25 at the rate of about 28.7 moles of cumene and 4.8 moles of α-methylstyrene per hour. This stream is typically hydrotreated to convert the α-methylstyrene portion to cumene, and the hydrotreated stream is then recycled to the oxidation phase of the overall process. Alternatively, this α-methylstyrene can be recovered as a by-product by conventional distillation means and the remaining cumene is recycled to the oxidation reactor.

It has heretofore been the general practice to provide one or more suitable vessels wherein the aqueous caustic phase, such as is recovered from the caustic wash column 23, is acid-treated and the sodium phenate contained therein is hydrolyzed and subsequently recovered as phenol. Pursuant to the processss of this invention, said aqueous phase is recycled and combined with the acid cleavage reaction mixture in line 1. It will be appreciated that utilization of this internal recycle stream in this manner will not only afford a reduced inventory of acid and caustic in the phenol recovery scheme, but also the elimination of one or more vessels. Accordingly, the aqueous caustic phase recovered from the bottom of the caustic wash column 23 through line 26 is combined with the aforementioned material recovered from the settler 20 through line 21, and the combined streams are continued through line 21 to be admixed with the acid cleavage reaction mixture in line 1 as heretofore described. It will be further appreciated that by operation of the neutralization and settler/separation vessels 3, 4, 9 and 10 at a temperature above 90° F., and preferably between 95° and 120° F., it is possible to minimize the water requirements in the neutralization stage thus decreasing the load on the effluent treatment section and, in addition, minimizing the flow of phenol and acetone to effluent treatment on account of the salting out effect accomplished by the higher saline concentration. Another benefit resulting from the operation at these temperatures is that any sodium sulfate that might accidentally crystallize out of the solution will do so as free flowing anhydrous sodium sulfate whereas, should the neutralization have been carried out at lower temperatures, the precipitate would have been in the form of sodium sulfate decahydrate which has a strong tendency to deposit on the walls as large crystalline needles and thus foul up the equipment.

I claim as my invention:

1. A process for the recovering of phenol from a reaction mixture resulting from the acid cleavage of cumene hydroperoxide and containing phenol, acetone, alphamethylstyrene, cumene and unreacted cumene, which process comprises the steps of:
   (a) effecting the neutralization of said reaction mixture by admixing an alkali metal phenate therewith at a temperature of from about 90° F. to about 120° F.;
   (b) recovering substantially all of said acetone by distillation from the neutralized reaction mixture;
   (c) separating the substantially acetone-free reaction mixture by distillation into a phenol fraction and a cumene-methylstyrene fraction containing residual phenol;
   (d) recovering said phenol fraction by withdrawal as a bottoms product from the last-mentioned distillation;
   (e) contacting the cumene-methylstyrene fraction with an alkali metal hydroxide and converting the residual phenol contained therein to an alkali metal phenate; and,
   (f) recycling said alkali metal phenate to the aforesaid neutralization of said acid cleavage reaction mixture.

2. The process of claim 1 further characterized in that said alkali metal hydroxide is sodium hydroxide and said alkali metal phenate is sodium phenate.

* * * * *